(12) United States Patent
Revel et al.

(10) Patent No.: US 8,617,887 B2
(45) Date of Patent: Dec. 31, 2013

(54) METHOD OF GENERATING OLIGODENDROCYTES FROM NEUROSPHERE CELLS

(75) Inventors: Michel Revel, Rehovot (IL); Judith Chebath, Rehovot (IL); Peter Lonai, Rehovot (IL); Rozemari Stirbu Lonai, legal representative, Rehovot (IL)

(73) Assignee: Yeda Research and Development Co. Ltd, Rehovot (IL)

( * ) Notice: Subject to any disclaimer, the term of this patent is extended or adjusted under 35 U.S.C. 154(b) by 0 days.

(21) Appl. No.: 10/560,294

(22) PCT Filed: Jun. 13, 2004

(86) PCT No.: PCT/IL2004/000507
§ 371 (c)(1),
(2), (4) Date: May 31, 2006

(87) PCT Pub. No.: WO2004/111210
PCT Pub. Date: Dec. 23, 2004

(65) Prior Publication Data
US 2007/0237748 A1    Oct. 11, 2007

(30) Foreign Application Priority Data

Jun. 12, 2003  (IL) .......................................... 156430
Dec. 7, 2003   (IL) .......................................... 159226

(51) Int. Cl.
*C12N 5/00* (2006.01)
*C12N 5/07* (2010.01)
*C12N 5/079* (2010.01)
*C12N 5/0797* (2010.01)
*C12N 5/0735* (2010.01)
*C12N 5/074* (2010.01)
*C12N 5/071* (2010.01)
*G01N 33/567* (2006.01)

(52) U.S. Cl.
USPC ........... 435/377; 435/368; 435/366; 435/326; 435/391; 435/392; 435/389; 435/384; 435/405; 435/408; 435/395; 435/396; 435/397; 435/398; 435/402; 435/401; 435/383

(58) Field of Classification Search
None
See application file for complete search history.

(56) References Cited

U.S. PATENT DOCUMENTS 6,562,619 B1 * 5/2003 Gearhart et al. ............... 435/366

FOREIGN PATENT DOCUMENTS

| WO | WO 00/78331 A2 | 12/2000 |
| WO | WO 01/88104 | * 11/2001 |
| WO | WO 02/086073 | * 10/2002 |
| WO | WO 03/059376 A1 | 7/2003 |

OTHER PUBLICATIONS

Shimazaki et al. J Neurosci. Oct. 1, 2001.; 21: 7642-53.*
MacDonald et al. J. Neurosci. Res. 2002. 68:255-264.*
Blight Nat. Neurosci. 2002. 5: 1051-4.*
Schmidt et al. Annu. Rev. Biomed. Eng. 2003. 5: 293-347.*
Hoke et al. Nat. Clin. Pract. Neurol. 2006: 448-454.*
Burgess et al. J of Cell Bio. 111:2129-2138, 1990.*
Bowie et al. Science, 1990, 247:1306-1310.*
Pawson et al. 2003, Science 300:445-452.*
Baumann et al. Physol. Rev. 2001. 81:871-927.*
Haggiag et al. FEBS Letters, 1999. 457: 200-204.*
Valerio et al. Mol. Cell Neurosci. 2002. 21: 602-615.*
Viswanathan et al.,"Ligand/Receptor Signaling Threshold (LIST) Model Accounts for gp130-Mediated Embryonic Stem Cell Self-Renewal Responses to LIF and HIL-6" Stem Cells, 20:119-138 (2002).
P. Zhang et al., Enhancement of Oligodendrocyte Differentiation from Murine Embryonic Stem Cells by an Activator of gp130 Signaling; Stem Cells, XP009035185, pp. 22:344-354; Rehovot, Israel, 2004.
O. Brüstle et al., Embryonic Stem Cell-Derived Glial Precursors: A Source of Myelinating Transplants; Science; XP-002292501; Bonn, Germany; Jul. 30, 1999; vol. 285.
F.H. Gage., Mammalian Neural Stem Cells; Stem Cell Research and Ethics; XP-002292502; La Jolla, California; vol. 287; Feb. 25, 2000.
N. Billon et al., Normal Timing of Oligodendrocyte Development from Genetically Engineered, Lineage-Selectable Mouse ES Cells; Journal of Cells Science 115 (18); XP-002292503; pp. 3657-3665, 2002.
J. Nichols et al., Derivation of Germline Competent Embryonic Stem Cells with a Combination of Interleukin-6 and Soluble Interleukin-6 Receptor; XP-002292519; Experimental Cell Research 215, 237-239 (1994), United Kingdom.
B. Stankoff et al., Ciliary Neurotrophic Factor (CNTF) Enhances Myelin Formation: A Novel Role for CNTF and CNTF-Related Molecules; The Journal of Neuroscience, Nov. 1, 2002, 22(21):9221-9227; Paris, France.
A. Valerio et al., A Soluble Interleukin-6 (IL-6) Receptor/IL-6 Fusion Protein Enhances the in Vitro Differentiation of Rat Oligodentrocytes; Abstract View; XP-001146998; Brescia, Italy, 2002.

* cited by examiner

*Primary Examiner* — Chang-Yu Wang
(74) *Attorney, Agent, or Firm* — Browdy and Neimark, PLLC

(57) ABSTRACT

The present invention is generally in the field of neurological diseases and disorders, particular in the field of neurodegenerative diseases in which the myelin cover of nerves is lost. IL6R/IL6 chimera is used to promote the formation of oligodendrocytes from embryonic stem cells for treatment of neurodegenerative diseases or posttraumatic nerve damage.

11 Claims, 2 Drawing Sheets

```
                        SEQUENCE LISTING

<160> NUMBER OF SEQ ID NOS: 3

<210> SEQ ID NO 1
<211> LENGTH: 13
<212> TYPE: PRT
<213> ORGANISM: Artificial
<220> FEATURE:
<223> OTHER INFORMATION: synthetic

<400> SEQUENCE: 1

Glu Phe Gly Ala Gly Leu Val Leu Gly Gly Gln Phe Met
1               5                   10

<210> SEQ ID NO 2
<211> LENGTH: 20
<212> TYPE: DNA
<213> ORGANISM: Artificial
<220> FEATURE:
<223> OTHER INFORMATION: synthetic

<400> SEQUENCE: 2
tgcgcgcgag aaggccgaag                                              20

<210> SEQ ID NO 3
<211> LENGTH: 19
<212> TYPE: DNA
<213> ORGANISM: Artificial
<220> FEATURE:
<223> OTHER INFORMATION: synthetic

<400> SEQUENCE: 3
cccagccagc cctcacttg                                               19
```

METHOD OF GENERATING OLIGODENDROCYTES FROM NEUROSPHERE CELLS

FIELD OF THE INVENTION

The present invention is generally in the field of neurological diseases and disorders. In particular it relates to neurodegenerative diseases in which the myelin cover of nerves is lost, as a result of degeneration of oligodendrocytes which are the cells producing the myelin in the central nervous system. More particularly, the present invention provides for the use of IL6R/IL6 chimera to promote the formation of oligodendrocytes from embryonic stem cells and as a medicament for treatment of neurodegenerative diseases or posttraumatic nerve damage.

BACKGROUND

Oligodendrocytes, which make the myelin sheaths in central nervous system (CNS), evolve from multipotential neural stem cells through a series of developmental stages (Rogister et al. 1999; Shihabuddin et al. 1999; Levine et al. 2001) for recent reviews). Recognized stages include early bipolar progenitors A2B5$^+$ cells, or O-2A (Raff 1989), late multipolar progenitors expressing the O4 sulfatide glycosides (Schachner et al. 1981), arborized immature oligodendrocytes O4 and GalC positive, and mature oligodendrocytes having the O1 sulfatide and synthesizing the myelin membrane with its structural components such as myelin basic protein (MBP).

Embryonic stem (ES) cell lines, derived from the inner cell mass of blastocyst-stage embryos, are a potential large scale source of oligodendrocytes and precursors derived from murine ES cell have been used for transplantion into myelin deficient CNS (Brustle et al. 1997; Brustle et al. 1999; McDonald et al. 1999). A number of culture conditions have been defined under which murine ES cells differentiated into floating embryoid bodies (EB) may be directed toward the neural lineages giving rise to various types of neurons, to astrocytes and to oligodendrocytes. One approach is based on selection in serum-free defined medium in which neural precursor cells survive, proliferate under the influence of basic fibroblast growth factor (FGF-2) and differentiate upon growth factor removal and plating on adherent substrates (Okabe et al. 1996). Under these conditions, some O4 positive cells develop provided tri-iodothyronine (T3) is added, in line with T3 effect on optic nerve derived O-2A progenitors (Barres et al. 1994). A more efficient selection is obtained by sequential treatment of EB cells by FGF-2, then FGF-2 with epidermal growth factor (EGF), and FGF-2 with Platelet derived growth factor PDGF-AA, a factor promoting proliferation of glial precursor cells (Besnard et al. 1987; Bogler et al. 1990), thereby increasing the number of A2B5$^+$ cells which after growth factors withdrawal differentiate into both O4$^+$ oligodendrocytes and astrocytes expressing glial fibrillary acidic protein GFAP (Brustle et al. 1999).

Another approach uses differentiation agents such as retinoic acid to induce neural and glial lineages in EB cultures (Bain et al. 1995; Fraichard et al. 1995). As in newborn brain derived cultures, neural precursors can be further enriched by selecting non-adherent cells growing as floating spheres in defined medium, and expanding them as neurospheres and oligodendrocyte-enriched oligospheres that differentiate after EGF, FGF removal (Zhang et al. 1998; Liu et al. 2000). Human ES cell lines derived EBs also form neural tube like rosettes expandable as floating neurospheres that can be transplanted in vivo or plated on polycationic substrates to differentiate into neurons, astrocytes and oligodendrocytes, the latter developing particularly after treatment with PDGF-AA and T3 (Reubinoff et al. 2001; Zhang et al. 2001). Although cytokines such as leukemia inhibitory factor (LIF) are known to maintain ES cells in an undifferentiated, multipotent state, it was recently found that LIF allows sparse murine ES cell cultures to develop into neurospheres (Tropepe et al. 2001).

Enriched murine ES cell derived oligospheres, yielding over 90% oligodendrocytes, have been obtained in a complex medium including combinations of hormones, such as T3 and progesterone, and cytokines such as Neurotrophin-3 (NT3) and ciliary neurotrophic factor CNTF (Liu et al. 2000). Both cytokines may contribute to an effect on oligodendrocyte precursors, as observed in optic nerve (Barres et al. 1994; Barres et al. 1996). However, the effects of CNTF on oligodendrocyte differentiation are not clear as in some conditions it mainly induces GFAP$^+$ astrocytes from A2B5$^+$ progenitors (or earlier glioblasts) with little effect on O4$^+$ cells (Lillien et al. 1990; Gard et al. 1995; Johe et al. 1996; Bonni et al. 1997), whereas in other conditions it also increases survival and proportion of GalC$^+$, O1$^+$ and MBP$^+$ cells in the cultures (Kahn et al. 1994; Mayer et al. 1994; Marmur et al. 1998).

CNTF belongs to the interleukin-6 (IL-6) family of cytokines that signal via gp130 either as a heterodimeric receptor with LIF-R (for CNTF, LIF, and oncostatin-M (OSM)) or as a homodimer (for interleukin-6 (IL-6), interleukin-11 (IL-11)) (Taga et al. 1997) for review). There is growing evidence on the importance of gp130 signaling for myelinating cells. In mice, postnatal gene deletion has indicated that gp130 is required to maintain Schwann cell function and myelination in peripheral nerves, in addition to its role in astrocytosis (Betz et al. 1998; Nakashima et al. 1999). With the help of a potent gp130 activating ligand, the IL6R/IL6 chimera in which IL-6 is fused to the extracellular portion of the IL-6 receptor (Chebath et al. 1997), we have previously observed induction of myelin gene expression in embryonic Schwann cells (Haggiag et al. 1999; Haggiag et al. 2001) and activation of myelin gene promoters (Slutsky et al. 2003). Activation of a transgenic MBP gene promoter in mice brain cultures was observed in response to CNTF (Stankoff et al. 2002) and in similar cortical cultures from newborn rat IL6R/IL6 chimera was more effective than CNTF to increase the development of highly arborized GalC+ oligodendrocytes (Valerio et al. 2002).

Promising results have been recently obtained in mice where injections of neural stem cells from the periventricular zone of adult mice brain and grown into neurospheres have induced clinical recovery and remyelination in an animal model of multiple sclerosis (Pluchino et al. 2003). Applying such technology to human patients suffering from multiple sclerosis or other demyelinating diseases, poses many difficulties because the neural stem cells would have to be isolated from cadavers or from aborted fetuses. Hence, the amount of cells that could be obtained would be limited, it would be difficult to ascertain that the brain cells do not transfer dangerous pathogens, and the transplants may cause problems of immuno-histocompatibility and may be rejected.

As indicated, blastocyst-derived ES cell lines, that are indefinitely expandable in laboratory tissue culture conditions, could provide a large-scale source of developing oligodendrocytes capable of myelinating neurons and thereby repairing lesions in the CNS (Cao et al. 2002; Gottlieb 2002).

Therefore, there is a need for a method to promote oligodendrocyte generation from ES cell lines.

SUMMARY OF THE INVENTION

The invention relates to a method for generating oligodendrocytes, suitable for repairing damage caused by demyelinating diseases, comprising growing embryonic stem (ES), embryoid bodies (EB) and/or neurosphere (NS) cells in the presence of one or more gp130 activators such as CNTF, OSM, IL-6, IL6R/IL6 chimera and IL-11.

In one aspect, the invention relates to the oligodendrocytes obtainable by the method of the invention and for their use in the manufacture of a medicament for treating damage caused by demyelinating diseases in a subject in need.

In another aspect, the invention relates to a use of an embryonic stem (ES), embryoid bodies (EB) and/or neurosphere (NS) cells and a gp 130 activator such as CNTF, OSM, IL-6, IL6R/IL6 chimera and IL-11, in the manufacture of a medicament for enhancing oligocytes differentiation for treating demyelinating diseases in a subject in need.

In a preferred embodiment of the invention, the gp 130 activator is an IL6R/IL6 chimera, a mutein, functional derivative, circularly permutated derivative, salt thereof or an active fraction such as IL-6.

In another preferred embodiment of the invention, the method uses embryonic stem cells such as neurosphere cells and dissociated neurosphere cells and more preferably embryoid bodies.

In a further preferred embodiment, the oligodendrocyte of the invention is of O1+ lineage and/or of O4+ lineage.

More specifically, the method of the invention relates to repairing damage caused by demyelinating diseases such as multiple sclerosis, stroke, spinal cord injury, neural trauma and demyelination of axon.

The invention provides a pharmaceutical composition comprising ES, EB and/or NS cells and one or more gp 130 activators selected from CNTF, OSM, IL-6, IL6R/IL6 chimera and IL-11.

In addition, the invention provides a pharmaceutical composition comprising ES, EB and/or NS cells and an expression vector encoding a gp 130 activator selected from CNTF, OSM, IL-6, IL6R/IL6 chimera and IL-11.

The invention further provides, a pharmaceutical composition comprising engineered ES, EB and/or NS cells producing one or more gp 130 activators selected from CNTF, OSM, IL-6, IL6R/IL6 chimera and IL-11.

More preferably, in the pharmaceutical composition of the invention the gp 130 activator is IL6R/IL6 chimera, a mutein, active fraction, circularly permutated derivative, salt thereof or functional derivative such as IL-6.

In one preferred embodiment of the invention cells such as e.g. dissociated NS cells.

In another preferred embodiment of the invention, the pharmaceutical composition comprises EB cells.

In yet another preferred embodiment of the invention, the pharmaceutical composition comprises the oligodendrocytes obtainable according to the method of the invention.

More specifically, the invention provides a pharmaceutical composition for treating damage caused by demyelinating diseases in a subject in need.

The invention also provides a culture medium suitable for promoting differentiation of embryonic stem (ES), embryoid bodies (EB) and/or neurosphere (NS) cells into oligodendrocytes comprising one or more gp 130 activators selected from CNTF, OSM, IL-6, IL6R/IL6 chimera and IL-11 in a solution suitable for culturing the cells.

In a preferred embodiment of the invention, the gp 130 activator is IL6R/IL6 chimera, a mutein, functional derivative, active fraction, circularly permutated derivative or salt thereof.

In another preferred embodiment of the invention, the gp 130 activator is IL-6.

In yet another preferred embodiment of the invention, the culture medium is suitable for promoting differentiation of embryonic stem such as EB and NS, into oligodendrocytes of O1+ lineage and/or of O4+ lineage.

The invention also provides a method of treatment of demyelinating diseases comprising the administration of an effective amount of the oligodendrocytes obtained according to the invention.

In one preferred embodiment of the invention, the oligodendrocytes of the invention are administered directly in the CNS of the subject in need.

The oligodendrocytes of the invention may be administered by IV injection to the subject in need.

The invention also provides a method of treating a demyelinating disease comprising the administration of ES, EB and/or NS cells and effective amount of one or more gp 130 activator selected from CNTF, OSM, IL-6, IL6R/IL6 chimera and IL-11 in a subject in need.

In one preferred embodiment in method of the invention, the gp 130 activator is an IL6R/IL6 chimera, a mutein, functional derivative, active fraction, circularly permutated derivative or salt thereof.

In another preferred embodiment of the method of the invention, the gp 130 activator is IL-6.

The embryonic cells may be NS cells such as dissociated NS cells and/or EB cells.

According to one embodiment of the method of the invention, the gp 130 activator is administrated by an expression vector.

The gp 130 activator may be also be administrated by a recombinant cell expressing the activator such as ES, EB and/or NS cells.

In a preferred embodiment of the method of the invention the gp 130 activator is contacted with the embryonic cells such as ES, EB and/or NS cells ex-vivo prior to administration.

the gp 130 activator and/or the cells may be administered directly in the CNS of the subject in need.

Preferably, the gp 130 activator and/or the cells are administered by IV injection of the subject in need.

Figure 1:
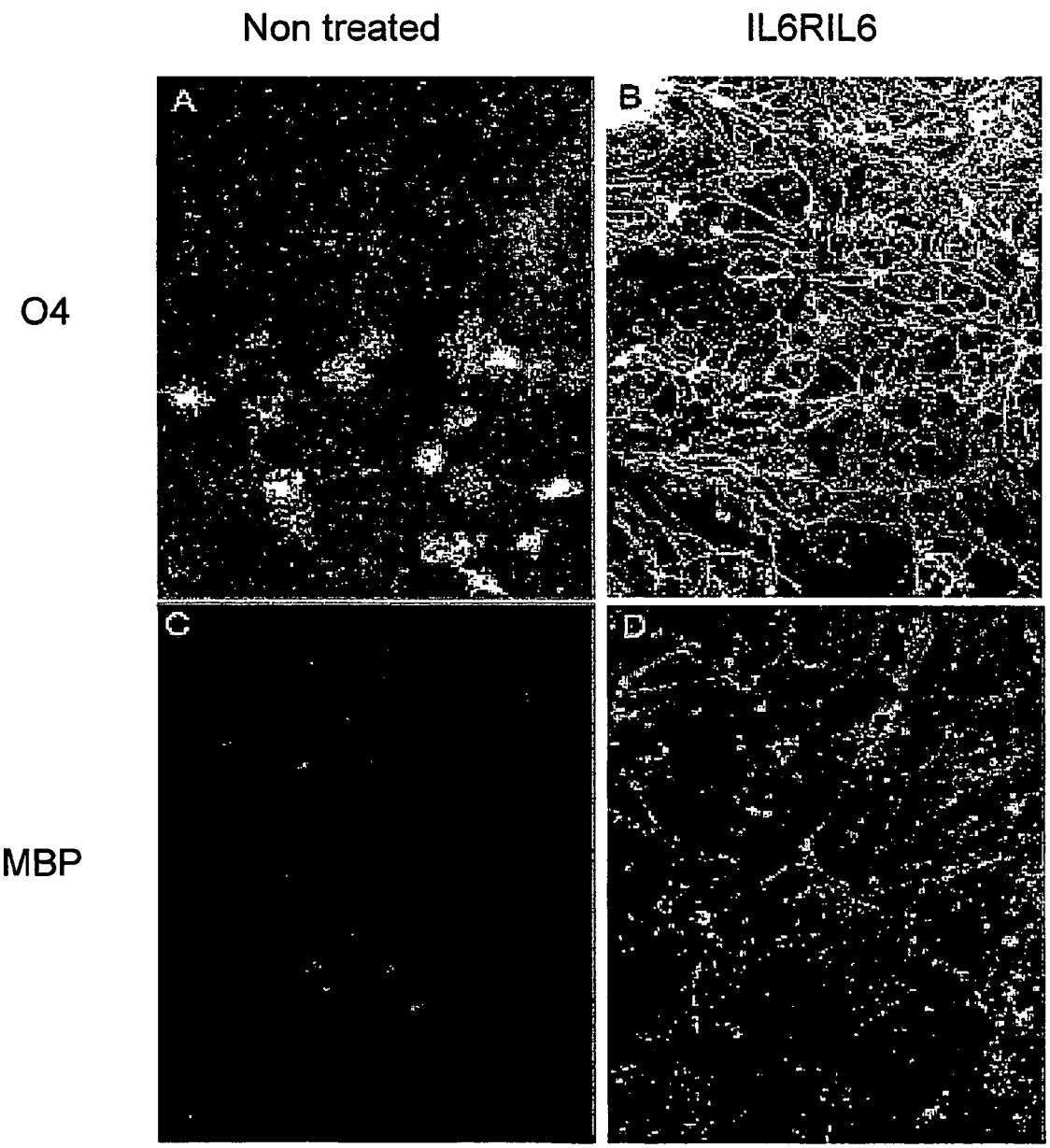
FIG. 1 shows fluorescent microphotographies of representative fields from murine ES cells (R11 cell line) that were grown into neurospheres and then cultured either without (non-treated) or with IL6R/IL6 chimera (200 ng/ml) for 6 weeks, at which time the cells were fixed and stained with antibodies specific for oligodendrocytes. The upper panels show staining with monoclonal antibody O4, which specifically detects a sulfatide glycoside present in immature or pre-oligodendrocytes. The lower panels show staining with anti-MBP antibodies against the myelin basic protein, which is a structural component of myelin formed only by mature oligodendrocytes. In the non-treated cultures, small $O4^+$ oligodendrocytes are observed whereas in the presence of IL6R/IL6 chimera there is a much more developed network of arborized oligodendrocytes, with long branches forming numerous neuronal contacts. In the IL6R/IL6 chimera-treated cultures, MBP is present in the branched network indicating the maturation of oligodendrocytes, contrasting with a weak staining of round and small cell bodies in the untreated cultures.

(Lanes 1,2): gene expression in spherical aggregates formed in EB cultures after selection for 12 days in defined medium with 20 ng/ml FGF-2. (Lanes 3-6): outgrowing neurospheres on PDL-FN for 8 days (FGF removed at day 4). Where indicated, IL6RIL6 was added for the last 4 days before extracting RNA. For lane 2, IL6RIL6 at 200 ng/ml and for lanes 4 and 6, IL6RIL6 at 100 ng/ml. Expression levels measured by RT-PCR are shown for GFAP (astrocyte lineage), for Olig-1 and Sox10 (early oligodendrocyte progenitors) and for MBP (oligodendrocyte maturation), versus the housekeeping gene G3'PDH as control for RNA loading.

DETAILED DESCRIPTION OF THE INVENTION

The invention relates to the use of a gp 130 activator, such as IL6R/IL6 chimera, for generating oligodendrocytes from embryonic stem (ES), embryoid bodies (EB) and/or neurosphere (NS) cells in order to increase myelination of nerves in injured central nervous system (CNS).

The invention further relates to a method for improving the potential of embryo stem (ES) cell cultures for subsequent transplantation and treatment in patients with neurodegenerative diseases caused by loss of the myelin sheaths around the nerves.

The invention relates to a culture medium suitable for promoting differentiation ES, EB and/or NS cells into oligodendrocytes wherein the culture medium comprise one or more gp130 activators and a solution suitable for culturing ES, EB and/or NS cells.

Specifically, the present invention can be used to treat neurodegenerative disorders such as multiple sclerosis, stroke, spinal cord injury, and other trauma, demyelination of axons (Gledhill et al. 1973; Griffiths et al. 1983; Blight 1985; Bunge et al. 1993). The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The use of cellular therapy is growing rapidly, and is gradually becoming an important therapeutic modality in treatment of various disorders for example, neuronal cell therapy for neurodegenerative diseases. Promising results have been recently obtained in mice where injections of neural stem cells from the periventricular zone of mice brain and grown into neurospheres have induced clinical recovery and remyelination in an animal model of multiple sclerosis (Pluchino et al. 2003). Applying such technology to human patients suffering from multiple sclerosis or other demyelinating diseases, poses many difficulties because the neural stem cells would have to be isolated from cadavers or from aborted fetuses. Hence, the amount of cells that could be obtained would be limited, it would be difficult to ascertain that the brain cells do not transfer dangerous pathogens, and the transplants may cause problems of immuno-histocompatibility and may be rejected.

The use of ES cells derived transplants has many advantages over the use of fetal or adult brain cells. The ES cells have high potential for expansion in vitro, can be ascertained to be pathogen-free and histocompatibility could be achieved by maintaining banks of ES cell lines (as done for bone marrow transplantation) or by cloning (i.e. producing ES cells from blastocysts produced by nuclear transfer from one of the patient's own cell) (Lanza et al. 1999). Experimental transplantation to animals has been successfully achieved with neurospheres derived from murine ES cells (Brustle et al. 1999; Liu et al. 2000) and from human ES cells (Reubinoff et al. 2001; Zhang et al. 2001). This approach could be greatly improved by having a method to promote the differentiation of ES cells toward specific cell lineages, such as myelinating oligodendrocytes.

In one embodiment of the invention, ES cells have been used to prepare neurospheres (by a procedure already used for human ES cells (Zhang et al. 2001)), and the neurosphere cells were then subjected to treatment by a pure recombinant human IL6R/IL6 chimera molecule produced in CHO cells (200 ng/ml) in a serum-free chemically defined medium (as described in example 1). In the presence of IL6R/IL6 chimera, the neurospheres that had been plated on poly-D-lysine and fibronectin developed a dense network of oligodendrocyte progenitors identified by the O4 sulfatide glycoside on their surface. In the cultures performed according to the state-of-the-art, without IL6R/IL6 chimera, only few and small oligodendrocytes developed. Hence, IL6R/IL6 chimera showed a specific effect on promoting the differentiation of the neurosphere cells toward the oligodendrocyte lineage.

In another embodiment it was shown that IL6R/IL6 chimera can lead to differentiation into oligodendrocyte progenitors (Rip+) also when administrated into short term cultures of ES cell-derived dissociated neurosphere cells (Example 3). Since progenitor cells may be better suited for transplantation than fully differentiated cells, this result supports the advantages of using IL6R/IL6 chimera to improve the ex-vivo preparation of cells that upon injection can migrate into the CNS and effect myelination.

It was also found that IL6R/IL6 chimera can lead to the maturation of oligodendrocytes that express structural components of myelin as the myelin basic protein MBP, and form myelin membranes typical of mature myelinating cells. This activity of IL6R/IL6 chimera indicates that it may be itself injected together with transplanted ES, EB and/or NS cells to promote their maturation in vivo and increase the efficacy of the repair of CNS demyelinating lesions.

The present invention embraces the use one or more gp130 activator, in the manufacture of a medicament for inducing generation of oligodendrocytes from ES, EB and/or NS cells. The gp130 activator may be added ex-vivo to cultures of ES, EB and/or NS cells, which are thereafter transplanted to a patient. Alternatively the gp130 activator could be injected to a patient before together or after injecting the cells in order to stimulate the in vivo differentiation of ES, EB and/or NS transplants. A preferred in vivo gp130 activator is IL-6 and more preferably IL6R/IL6 chimera. IL6R/IL6 chimera may also be applied for stimulating the generation of oligodendrocytes early progenitors from ES, EB and/or NS cells. Additional gp130 activators according to the invention are selected from LIF, CNTF, CT-1, OSM, IL-6 and IL-11.

ES cells according to the invention are any cells that are pluripotent, capable of producing progeny that are derivatives of all three germline layers, regardless of whether they were derived from embryonic tissue, fetal tissue, or other sources. In particular, embryonic stem cells (ES) from primates comprise various types of cells, e.g. human embryonic stem (hES)

cells, described by Thomson et al. (Thomson et al. 1998); embryonic stem cells from other primates, such as Rhesus stem cells (Thomson et al. 1995), marmoset stem cells (Thomson et al. 1996) and human embryonic germ (hEG) cells (Shamblott et al. 1998).

Embryonic stem (ES) cell lines for the use according to the invention can be obtained from blastocyst-stage embryos (Brustle et al. 1997; Brustle et al. 1999; McDonald et al. 1999). Traditionally, ES cells are cultured on a layer of feeder cells, typically fibroblasts derived from embryonic or fetal tissue. To prepare a feeder cell layer, cells are irradiated or otherwise treated to inhibit proliferation but permit synthesis of factors that support ES cells. LIF or related cytokines are often added to maintain ES pluripotency.

Culture conditions inducing the progression of such ES cells through a series of transitions that may culminate in the generation of functional differentiated neuronal and glial cells comprise the following steps: 1—expansion of undifferentiated ES cells, 2—generation of embryoid bodies that include primitive endoderm and ectoderm layers, 3—culturing embryoid bodies to select for neurospheres in defined medium with one or more growth factors, typically bFGF, 4—expanding the neurospheres in suspension, 5—induction of differentiation of the expanded neurospheres by the withdrawal of growth factors and/or by growing in adherent conditions.

The cells according to the present invention comprise cells derived from any one of the above five steps.

Embryoid bodies can be generated in suspension culture according to the method described by Martin et al., (1975) "Differentiation of clonal lines of teratocarcinoma cells: Formation of embryoid bodies in vitro," (Martin et al. 1975).

Briefly, to form embryoid bodies, the clusters of ES cells are disengaged from the tissue culture plates. Methods for disengaging cells from tissue culture plates are known and include the use of enzymes, such as trypsin or papain, dispase or commercially available preparations.

Generally, the ES cells disengage from the tissue culture plates in clusters (e.g., aggregates of 10 to 50 or more cells). The clusters of ES cells are then dissociated to obtain a population of cells which includes a majority of individual cells. Methods for dissociating clusters of cells are likewise known. One method for dissociating clusters of cells includes mechanically separating the cells, for example, by repeatedly aspirating a cell culture with a pipet. Preferably, the ES cells are in an exponential growth phase at the time of dissociation to avoid spontaneous differentiation that tends to occur in an overgrown culture.

The dissociated ES cells are then cultured in ES1 media as described below. However, in contrast to the ES cell proliferation stage (in which the cells are grown on a tissue culture dish surface), the embryoid bodies can be generated in suspension. For example, the cells may be cultured on non-adherent bacterial culture dishes. In this stage, the cells are incubated for about 4 days to about 7 days. Preferably, the medium is changed every 1 to 3 days.

A number of specific culture conditions for ES cells differentiation from embryoid bodies (EB) were described and are incorporated inhere by reference.

One approach is based on selection in serum-free defined medium in which neural precursor cells survive, proliferate under the influence of basic fibroblast growth factor (FGF-2) and differentiate upon growth factor removal and plating on adherent substrates (Okabe et al. 1996). Under these conditions, some O4 positive oligodendrocyte precursor cells develop when tri-iodothyronine (T3) is added, in line with T3 effect on optic nerve derived O-2A progenitors (Barres et al. 1994).

EB cultures can be obtained also by another approach, which uses differentiation agents such as retinoic acid to induce neural and glial lineages in EB cultures (Bain et al. 1995; Fraichard et al. 1995).

As in newborn brain derived cultures, neural precursors can be further enriched by selecting non-adherent cells growing as floating spheres in defined medium, and expanding them as neurospheres and oligodendrocyte-enriched oligospheres that differentiate after EGF, FGF removal (Reynolds et al. 1996; Zhang et al. 1998; Liu et al. 2000). Human ES cell lines derived EBs also form neural tube like rosettes expandable as floating neurospheres that can be transplanted in vivo or plated on polycationic substrates to differentiate into neurons, astrocytes and oligodendrocytes, the latter developing particularly after treatment with PDGF-AA and T3 (Reubinoff et al. 2001; Zhang et al. 2001).

Any commercial growth medium, or cell formulation, suitable for culturing embryonic stem cells (e.g. ES-Cult™ medium from StemCell Technologies) can be employed in the present invention. Non limiting examples for solutions suitable for culturing the cells of the invention comprise Dulbecco's DMEM (preferably high glucose about 4.5 mg/ml) (Gibco/BRL) with about 0.1 mM non-essential amino acids, 1-5 mM glutamine or about 0.5 g/liter, 0.5-5 mM sodium pyruvate or about 0.11 g/liter, 0.01-0.5 mM or about 0.01 g/liter β-mercaptoethanol, 2-20% fetal calf serum (FCS) and optionally 100 U/ml penicillin, 0.1 mg/ml streptomycin, and about 40 mg/ml leukemia inhibitory factor LIF, or DMEM high glucose (preferably high glucose about 4.5 mg/ml), 5-20% newborn calf serum (heat-inactivated), 1-5 mM or about 0.5 g/liter glutamine, and optionally 50 U/ml penicillin, 50 μg/ml streptomycin, or DMEM/F12 (1:1), 2-20% FCS, 1-5 mM or about 0.5 g/liter or 0.5-2% glutamine, 0.01-0.5 mM β-mercaptoethanol, 0.5-5 μg/ml heparin and 1-10 ng/ml FGF-2 or serum-free defined medium comprising DMEM/F12 with 1-50 μg/ml insulin, 10-200 mg/ml transferrin, 10-100 μM putrescine, 5-100 nM or 0.01 mg/l sodium selenite, 0.5-10 μg/ml heparin, 2-200 nM progesterone and 0-100 ng/ml of FGF-2 or DMEM/F12 with 1-10 μg/ml insulin, 10-200 μg/ml transferrin, 1-50 μg/ml putrescine, 0-50 ng/ml selenite and 1-20 ng/ml progesterone, and optionally 50 μg/ml ascorbic acid (Vitamin C).

In one embodiment of the present invention the ES cell line R11 is cultured for 3 days on a feeder layer in ES medium (see example 1 below) containing LIF. Cells are subcultured with trypsin, seeded and cultured for 2 days in ES1 medium (see example 1 below) lacking LIF but containing FGF. To induce embryoid bodies cells are detached from the feeder layer with dispase and cultured in ES1 medium without FGF for 4 days. The clumps (embryoid bodies, EB) were picked and cultured in serum free, chemically-defined EB medium (see example 1 below) supplemented with FGF for 8-10 days. The neurospheres produced were picked and transferred to non-adherent bacterial culture dishes in which the spheres grew in suspension for 7 days in EB medium supplemented with FGF. Following this step the neurospheres (NS) were transferred to fibronecting coated plates to grow in adherent mode employing defined differentiation medium.

A similar procedure can be employed using human ES cells to obtain EB and/or NS cells as described (Reubinoff et al. 2001; Zhang et al. 2001).

According to the present invention, a gp130 activator is added to the cultures of ES, EB and/or NS cells to promote formation of oligodendrocyte progenitors, or the gp130 activator with ES, EB and/or NS cells are administered to a patient suffering from demyelinating disease to enhance oligodendrocyte differentiation of ES, EB and/or NS cells, either alone or together with other growth or differentiation agents such as retinoic acid, EGF, PDGF etc.

It will be appreciated that ES cells are also available commercially and can be used according to this aspect of the present invention. Human ES cells can be purchased, e.g. from the NIH human embryonic stem cells registry (<http:escr.nih.gov>).

The cells with gp130 activator according to the invention can be implanted directly in the CNS or can be injected, for example intravenously (IV), and allowed to migrate to the CNS.

A preferred gp130 activator in accordance with the present invention is IL-6, and more preferred IL6R/IL6 chimera, which is active even in cells that have only gp130 on their surface and lack other receptors of the IL-6 cytokine family. An "IL6R/IL6 chimera" (also called "IL6R/IL6" or "IL-6 chimera"), as used herein, is a chimeric molecule comprising a soluble part of the interleukin-6 receptor fused to all or a biologically active fraction of interleukin-6. The moieties of the chimeric protein can be fused directly, or they can be linked by any suitable linker, such as a disulfide bridge or a polypeptide linker. The linker may be a short linker peptide, which can be as short as 1 to 3 amino acid residues in length or longer, for example, 13 or 18 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met (SEQ ID NO:1) introduced between the amino acid sequence of the soluble IL-6 receptor and the IL-6 sequence. Examples of IL6R/IL6 chimeric molecules are known in the art and have been described in detail e.g. in WO 99/02552 or WO 97/32891.

The IL6R/IL6 chimera may be produced in any adequate eukaryotic or prokaryotic cell type, such as yeast cells, insect cells, bacteria, and the like. It is preferably produced in mammalian cells, most preferably in genetically engineered CHO cells as described in WO 99/02552. Whilst the protein from human origin is preferred, it will be appreciated by the person skilled in the art that a similar fusion protein of any other origin may be used according to the invention, as long as it retains the biological activity described herein.

The delivery of IL6R/IL6 chimera to the brain may also be carried out using a vector comprising the coding sequence or an IL6R/IL6 chimera, a mutein, fused protein, active fraction or circularly permutated derivative thereof. The vector comprises all regulatory sequences needed for expression of the desired protein in the human body, preferably in the brain, more preferably in the striatum. Regulatory sequences for expression vectors are known by the person skilled in the art. The invention thus also relates to the use of a vector comprising the coding sequence of IL6R/IL6 chimera for manufacture of a medicament for the treatment of CNS injuries.

Any expression vector known in the art may be used according to the invention. However, a lentivirally-derived vector may be particularly useful for the delivery of IL6R/IL6 chimera directly into the striatum. Such lentiviral vectors are known in the art. They are specifically described e.g. in (Kordower et al. 1999; Deglon et al. 2000; Bensadoun et al. 2001).

Alternatively, the ES cells of the present invention can be contacted with gp 130 activator expressing and optionally presenting cells (i.e., insoluble-membrane bound gp 130 activator). This can be effected by co-culturing the stem cells of the present invention with cells, which express a secreted or membrane-bound gp 130 activator. For example, fibroblast feeder cells, which are oftentimes-co-cultured with stem cells to support proliferation thereof in a non-differentiated state can express an gp 130 activator of interest, thereby performing a dual role i.e., growth support and increase differentiation of ES into oligodendrocytes.

Alternatively, the ES cells of the present invention can be transformed with an expression construct such as that described below in order to express the gp 130 activator or the active portion thereof in the ES cells.

In such cases, the expression construct includes a cis-acting regulatory element active in mammalian cells (examples below). The nucleic acid construct of the present invention can further include an enhancer, which can be adjacent or distant to the promoter sequence and can function in up regulating the transcription therefrom.

As mentioned the preferred gp 130 activator is IL6R/IL6 chimera or a mutein, isoform, fused protein, functional derivative, active fraction, circularly permutated derivative or salt thereof and can be used for the manufacture of a medicament for the generation of oligodendrocytes from ES cells for the treatment of CNS injuries.

The terms "treating" as used herein should be understood as preventing, inhibiting, attenuating, ameliorating or reversing any or all symptoms or cause(s) of demyelinating neurodegenerative diseases.

As used herein the term "muteins" refers to analogs of an IL6R/IL6 chimera, in which one or more of the amino acid residues of the naturally occurring components of IL6R/IL6 chimera are replaced by different amino acid residues, or are deleted, or one or more amino acid residues are added to the original sequence of an IL6R/IL6 chimera, without changing considerably the activity of the resulting products as compared with the original IL6R/IL6 chimera. These muteins are prepared by known synthesis and/or by site-directed mutagenesis techniques, or any other known technique suitable therefore.

Muteins in accordance with the present invention include proteins encoded by a nucleic acid, such as DNA or RNA, which hybridizes to DNA or RNA, which encodes an IL6R/IL6 chimera, in accordance with the present invention, under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al. (Sambrook, J. C., Fritsch, E. F., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Any such mutein preferably has a sequence of amino acids sufficiently duplicative of that of an IL6R/IL6 chimera, such as to have substantially similar, or even better, activity to IL6R/IL6 chimera.

One characteristic activity of IL6R/IL6 chimera is its capability of binding to gp130. An ELISA type assay for measuring the binding of IL6R/IL6 chimera to gp130 has been described in detail in example 7 on page 39 of WO 99/02552, which is fully incorporated by reference herein. As long as the mutein has substantial binding activity to gp130, it can be considered to have substantially similar activity to IL6R/IL6 chimera. Thus, it can be determined whether any given mutein has at least substantially the same activity as IL6R/IL6 chimera by means of routine experimentation comprising subjecting such a mutein, e.g., to a simple sandwich binding assay to determine whether or not it binds to an immobilized gp130, as described in example 7 of WO 99/02552.

In a preferred embodiment, any such mutein has at least 40% identity or homology with the amino acid sequence of IL6R/IL6 chimera comprised in WO 99/02552. More preferably, it has at least 50%, at least 60%, at least 70%, at least 80% or, most preferably, at least 90% identity or homology thereto.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "percent identity" may be determined. In general, the two sequences to be compared are aligned to give a maximum correlation between the sequences. This may include inserting "gaps" in either one or both sequences, to enhance the degree of alignment. A percent identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al 1984, Nucleic Acids Res. 1984 Jan. 11; 12(1 Pt 1):387-95.), for example the programs BESTFIT and GAP, may be used to determine the % identity between two polynucleotides and the % identity and the % homology between two polypeptide sequences. BESTFIT uses the "local homology" algorithm of Smith and Waterman (J Theor Biol. 1981 Jul. 21;91(2):379-80 and J Mol. Biol. 1981 Mar. 25; 147(1):195-7. 1981) and finds the best single region of similarity between two sequences. Other programs for determining identity and/or similarity between sequences are also known in the art, for instance the BLAST family of programs (Altschul S F et al, 1990 J Mol. Biol. 1990 Oct. 5; 215(3):403-10, Proc Natl Acad Sci USA. 1990 July; 87(14):5509-13, Altschul S F et al, Nucleic Acids Res. 1997 Sep. 1; 25(17):3389-402, accessible through the home page of the NCBI at www.ncbi.nlm.nih.gov) and FASTA (Pearson W R, Methods Enzymol. 1990; 183:63-98. Pearson J Mol. Biol. 1998 Feb. 13; 276(1):71-84).

Muteins of IL6R/IL6 chimera, which can be used in accordance with the present invention, or nucleic acid coding therefore, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of IL6R/IL6 chimera may include synonymous amino acids within a group which have sufficiently similar physicochemical properties that substitution between members of the group will preserve the biological function of the molecule (Grantham Science. 1974 Sep. 6; 185(4154):862-4). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table 1. More preferably, the synonymous amino acid groups are those defined in Table 2; and most preferably the synonymous amino acid groups are those defined in Table 3.

TABLE 1

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE 2

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE 3

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of IL6R/IL6 chimera polypeptides, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

"Functional derivatives" as used herein cover derivatives of IL6R/IL6 chimera, and their muteins, which may be prepared from the functional groups which occur as side chains on the residues or are additions to the N- or C-terminal groups, by means known in the art, and are included in the invention as long as they remain pharmaceutically acceptable, i.e. they do not destroy the activity of the protein which is substantially similar to the activity of IL6R/IL6 chimera, and do not confer toxic properties on compositions containing it.

These derivatives may, for example, include polyethylene glycol side-chains, which may mask antigenic sites and extend the residence of an IL6R/IL6 chimera in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carboxylic aroyl groups) or O-acyl derivatives of free hydroxyl groups (for example that of seryl or threonyl residues) formed with acyl moieties.

An "active fraction" according to the present invention may e.g. be a fragment of IL6R/IL6 chimera. The term fragment refers to any subset of the molecule, that is, a shorter peptide that retains the desired biological activity. Fragments may readily be prepared by removing amino acids from either end of the IL6R/IL6 chimera molecule and testing the resultant fragment for its properties to bind to gp130. Proteases for removing one amino acid at a time from either the N-terminal or the C-terminal of a polypeptide are known, and so determining fragments, which retain the desired biological activity, involves only routine experimentation.

As active fractions of an IL6R/IL6 chimera, muteins and fused proteins thereof, the present invention further covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to gp130.

The term "salts" herein refers to both salts of carboxyl groups and to acid addition salts of amino groups of the IL6R/IL6 chimera molecule or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of IL6R/IL6 chimera, i.e., the ability to bind to gp130.

The term "circularly permuted" as used herein refers to a linear molecule in which the termini have been joined together, either directly or through a linker, to produce a circular molecule, and then the circular molecule is opened at another location to produce a new linear molecule with termini different from the termini in the original molecule. Circular permutations include those molecules whose structure is equivalent to a molecule that has been circularized and then opened. Thus, a circularly permuted molecule may be synthesized de novo as a linear molecule and never go through a circularization and opening step. The particular circular permutation of a molecule is designated by brackets containing the amino acid residues between which the peptide bond is eliminated. Circularly permuted molecules, which may include DNA, RNA and protein, are single-chain molecules, which have their normal termini fused, often with a linker, and contain new termini at another position. See Goldenberg, et al. J. Mol. Biol., 165: 407-413 (1983) and Pan et al. Gene 125: 111-114 (1993), both incorporated by reference herein. Circular permutation is functionally equivalent to taking a straight-chain molecule, fusing the ends to form a circular molecule, and then cutting the circular molecule at a different location to form a new straight chain molecule with different termini. Circular permutation thus has the effect of essentially preserving the sequence and identity of the amino acids of a protein while generating new termini at different locations.

In a preferred embodiment of the invention, the IL6R/IL6 chimera is glycosylated at one or more sites.

A glycosylated form of an IL6R/IL6 chimera has been described in WO 99/02552 (PCT/IL98/00321), which is the chimeric molecule highly preferred according to the invention. The IL6R/IL6 chimera described therein is a recombinant glycoprotein, which was obtained fusing the entire coding sequence of the naturally occurring soluble IL-6 receptor δ-Val (Novick et al. 1990) to the entire coding sequence of mature naturally occurring IL-6, both from human origin.

The IL6R/IL6 chimera may be produced in any adequate eucaryotic or procaryotic cell type, like yeast cells, insect cells, bacteria, and the like. It is preferably produced in mammalian cells, most preferably in genetically engineered CHO cells as described in WO 99/02552. Whilst the protein from human origin is preferred, it will be appreciated by the person skilled in the art that a similar fusion protein of any other origin may be used according to the invention, as long as it retains the biological activity described herein.

Advantageously, the chimeric molecule can then be produced in bacterial cells, which are not capable of synthesizing glycosyl residues, but usually have a high yield of produced recombinant protein.

Functional derivatives of IL6R/IL6 chimera may be conjugated to polymers in order to improve the properties of the protein, such as the stability, half-life, bioavailability, tolerance by the human body, or immunogenicity.

Therefore, a preferred embodiment of the invention relates to a functional derivative of the IL6R/IL6 chimera comprising at least one moiety attached to one or more functional groups, which occur as one or more side chains on the amino acid residues.

A highly preferred embodiment relates to an IL6R/IL6 chimera linked to Polyethlyenglycol (PEG). PEGylation may be carried out by known methods, such as the ones described in WO 92/13095, for example.

The IL6R/IL6 chimera may be delivered to the brain in any adequate formulation. It may also be delivered in form of cells expressing and/or secreting an IL6R/IL6 chimera, a mutein, fused protein, active fraction or circularly permutated derivative thereof.

The invention therefore further relates to the use of ES cells and IL6R/IL6 chimera, a mutein, fused protein, active fraction or circularly permutated derivative thereof, for manufacture of a medicament for the treatment of CNS injuries. The cells may be administered in any suitable form. However, a polymer-encapsulated cell is a highly preferred mode of delivery of the cells. The encapsulation procedure is described in detail e.g. by Emerich et al (J Comp Neurol. 1994 Nov. 1; 349(1):148-64 and Exp Neurol. 1994 Nov.; 130(1): 141-50.) or U.S. Pat. No. 5,853,385. Suitable cell lines and stable expression systems are well known in the art.

The delivery of IL6R/IL6 chimera to the brain may also be carried out using a vector comprising the coding sequence or an IL6R/IL6 chimera, a mutein, fused protein, active fraction or circularly permutated derivative thereof. The vector comprises all regulatory sequences needed for expression of the desired protein in the human body, preferably in the brain, more preferably in the striatum. Regulatory sequences for expression vectors are known by the person skilled in the art. The invention thus also relates to the use of a vector comprising the coding sequence of IL6R/IL6 chimera for manufacture of a medicament for the treatment of demyelinating diseases.

Any expression vector known in the art may be used according to the invention. However, a lentivirally-derived vector may be particularly useful for the delivery of IL6R/IL6 chimera directly into the striatum. Such lentiviral vectors are known in the art. They are specifically described e.g. in Kordower et al. (1999) or Déglon et al. (2000).

It is a further object of the present invention to provide a pharmaceutical composition comprising IL6R/IL6 chimera, a mutein, fused protein, functional derivative, active fraction, circularly permutated derivative or salt thereof, optionally together with one or more pharmaceutically acceptable carriers, diluents or excipients, for the treatment of CNS injury. The IL6R/IL6 chimera used may be either from eukaryotic origin (glycosylated) or from bacterial origin (non-glycosylated).

The invention further relates to a pharmaceutical composition comprising IL6R/IL6 chimera, to a pharmaceutical composition comprising an expression vector, in particular a lentiviral gene therapy vector expressing IL6R/IL6 chimera and to pharmaceutical composition comprising in addition to the IL6R/IL6 chimera (protein or vector) ES cells optionally together with one or more pharmaceutically acceptable carriers, diluents or excipients, for the treatment of CNS injury.

The pharmaceutical composition, according to the invention, may comprise a mixture of gp 130 activators.

The definition of "pharmaceutically acceptable" is meant to encompass any carrier, which does not interfere with effectiveness of the biological activity of the active ingredient and that is not toxic to the host to which it is administered. For example, for parenteral administration, IL6R/IL6 chimera may be formulated in a unit dosage form for injection in vehicles such as saline, dextrose solution, serum albumin and Ringer's solution.

The IL6R/IL6 chimera can be administered to a patient in need in a variety of ways. The routes of administration include intracranial, intradermal, transdermal (e.g. in slow release formulations), intramuscular, intraperitoneal, intravenous, subcutaneous, oral, epidural, topical, and intranasal routes. Any other therapeutically efficacious route of administration can be used, for example absorption through epithelial or endothelial tissues or by gene therapy wherein a DNA molecule encoding the IL6R/IL6 chimera is administered to the patient (e.g. via a vector), which causes the IL6R/IL6 chimera to be expressed and secreted in vivo. In addition the IL6R/IL6 chimera can be administered together with other components of biologically active agents such as pharmaceutically acceptable surfactants, excipients, carriers, diluents and vehicles.

For parenteral (e.g. intravenous, subcutaneous, intramuscular) administration, IL6R/IL6 chimera can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

It is a further object of the present invention to provide for a method for treating demyelinating diseases, comprising administering to a patient in need thereof an effective amount of IL6R/IL6 chimera, a mutein, fused protein, functional derivative, active fraction, circularly permutated derivative or salt thereof optionally together with a pharmaceutically acceptable carrier and effective amount of ES, EB, NS and/or derived cells.

An "effective amount" refers to an amount of the active ingredients that is sufficient to affect the course and the severity of the diseases described above, leading to the reduction or remission of such pathology. The effective amount will depend on the route of administration and the condition of the patient.

The dosage administered, as single or multiple doses, to an individual will vary depending upon a variety of factor, including IL6R/IL6 chimera pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled.

A method for treating demyelinating diseases, comprise administering to a patient in need thereof an effective amount of IL6R/IL6 chimera, a mutein, fused protein, active fraction or circularly permutated derivative thereof, or comprising administering to a patient in need thereof an expression vector comprising the coding sequence of IL6R/IL6 chimera, a mutein, fused protein, active fraction or circularly permutated derivative thereof, and ES cells.

It is a further object of the present invention to provide for a method for the preparation of differentiated oligodendrocytes for transplantation into patients in order to repair damage caused by demyelinating diseases. The IL6R/IL6 chimera will in this case be used ex-vivo to stimulate the development of oligodendrocytes from ES cells. Such stimulation can greatly improve the yield of oligodendrocyte cells from in vitro cultures, facilitating the use of these tissues for subsequent transplantation.

The present invention will now be described in more detail in the following non-limiting examples and the accompanying drawings.

EXAMPLES

Example 1

IL6R/IL6 Chimera Enhances the Differentiation of Oligodendrocyte Progenitors Expressing the O4 Sulfatide The murine ES cell line Rosa 11 (R11) (Li et al. 2001) was seeded at $0.7 \times 10^6$ cells/6 cm dish on top of feeder layer of γ-irradiated embryo fibroblasts (see below) in 5 ml of ES medium comprised of Dulbecco's DMEM high glucose (4.5 mg/ml) (Gibco/BRL) with 0.1 mM non-essential amino acids, 2 mM glutamine, 1 mM sodium pyruvate, 0.1 mM β-mercaptoethanol, 100 U/ml penicillin, 0.1 mg/ml streptomycin, 15% fetal calf serum (FCS) and 40 mg/ml leukemia inhibitory factor LIF, and cultured 3 days. All cultures were at 37° C. in 6.5% $CO_2$, with daily replacement of medium. The feeder cells were obtained by trypsinisation of 15.5 day old mouse embryos, cultured at $5 \times 10^6$ cells/10 cm plate in 10 ml of DMEM high glucose (4.5 mg/ml), 10% newborn calf serum (heat-inactivated at 56° C., 0.5 hour), 2 mM glutamine, 50 U/ml penicillin, 50 µg/ml streptomycin, trypsinized and suspended in 5 ml of same medium for γ-irradiation from a cobalt source at 3000 rad for 10.5 minutes, and then plated at $0.3 \times 10^6$ cells/6 cm dish.

After 3 days, the R11 ES cells were subcultured with 0.05% trypsin and seeded as above but in ES1 medium comprising DMEM/F12 (1:1), 15% FCS, 1% glutamine, 0.1 mM β-mercaptoethanol, 2 µg/ml heparin and 4 ng/ml FGF-2. After 2 days, the ES cells treated with 0.2 mg/ml dispase (Gibco/BRL) at 37° C. for 15 minutes, and the detached cell clusters were washed and cultured in 3 tissue culture (Nunclon) 9 cm-plates with 10 ml of medium ES1 but without FGF, for 4 days during which embryoid bodies (EB) developed. These were then treated with 0.1 mg/ml dispase (10 min 37° C.) and the dislodged EBs were picked and transferred to new plates (about 50/25 cm$^2$) in serum-free defined EB medium comprising DMEM/F12 with 25 µg/ml insulin, 100 µg/ml transferrin, 60 µM putrescine, 30 nM sodium selenite, 2 µg/ml heparin, 20 nM progesterone and 20 ng/ml of FGF-2, and cultured 8-10 days with daily medium change. The cultures were again partially dissociated with 0.1 mg/ml dispase (10 min 37° C.) and ~200 spherical clumps (identified as neurospheres, NS, by the outgrowth of axons) were picked and transferred into non-adherent bacterial culture Petri dishes (9 cm with 10 ml of the same EB medium) in which the spheres grew in suspension for 7 days.

The neurospheres were deposited on individual glass cover slips that had been coated with a solution of 20 µg/ml poly-D-lysine (Sigma, St Louis, Mo.)), applied overnight at 37° C. in 5% $CO_2$, washed in water and dried before adding 250 µg/ml fibronectin for 2-12 hours at 4° C. About 4 neurospheres were placed on each coated coverslip, which were put at the bottom of each well of 12-well plates in 1 ml of defined differentiation medium containing DMEM/F12 with 5 µg/ml insulin, 100 µg/ml transferrin, 16.1 µg/ml putrescine, 5.2 ng/ml selenite and 6.3 ng/ml progesterone (supplied as 1% N2 supplement, Gibco/BRL). Half of the wells were supplemented with pure IL6R/IL6 chimera, 200 ng/ml (volume of stock added to each well) (produced in CHO cells as described in (Chebath et al. 1997)). The medium and all its ingredients were replaced every 3 days and after 3 weeks 50 µg/ml ascorbic acid (Vitamin C) was added to the medium and the culture continued. At 6 weeks after plating the neurospheres, the cultures were fixed in 4% paraformaldehyde and kept in PBS at 4° C. Before immunostaining, the plates were blocked with 5% FCS in PBS for 30 min at 22° C. Staining for immature oligodendrocytes was done with anti-sulfatide O4 monoclonal antibodies (Chemicon, Temecula, Calif.; used at 1:75 for 60 min at 37° C.) and FITC-conjugated anti-IGM polyclonal antibodies (at 1:50 for 60 min at 37° C.). Monoclonal antibody TuJ-1 anti-tubulin beta III (Covance Research Products, Berkeley, Calif., diluted 1:400) was used to stain the axonal network. Astrocytes were stained with monoclonal anti glial fibrillary acid protein (GFAP) conjugated with the fluorescent tag Cy3 (Sigma, St Louis, Mo.), 1:400). After washing with PBS 3 times for 5 min, the secondary antibody, FITC- or Cy3-conjugated goat anti-mouse IgG or IgM (Jackson ImmunoResearch Lab, Inc, 1:400 in PBS) was added and left for 1 h at room temperature, before washing with PBS 3 times for 5 minutes, and mounting in Mowiol (Calbiochem, LaJolla, Calif.). Samples were examined with a microscope Olympus IX-70 FLA under UV-light fluorescence. Photographs were made with a microscope mounted DVC digital camera and were processed in Photoshop.

Using the above procedure, the effect of IL6R/IL6 chimera on neurospheres cell differentiation was studied. In brief, murine R11 ES cells, which had been subcultured on a feeder layer of irradiated embryo fibroblasts in medium with serum and FGF-2, were removed from the feeder layer, cultured 4 days in tissue culture dishes without FGF-2 and the resulting EBs were dissociated and re-plated in serum-free defined medium with 20 ng/ml FGF-2 for 8 days. As described (Zhang et al. 2001), rosette-type clumps that may represent neural tube-like structures appeared and were dislodged by partial digestion with dispase to be transferred as suspension cultures in non-adherent plates in the same medium. Within a week, the clumps grew to form neurospheres that were picked and adhered onto glass cover slips coated with poly-D-lysine and fibronectin, a substrate that favors glial cell development (Reubinoff et al. 2001). Numerous neuronal processes grew out of the spheres, forming axonal bundles that were visualized by immunostaining for βIII-tubulin. At 3 weeks, the axonal network was comparable in the outgrowth of neurospheres plated either with or without IL6R/IL6 chimera (not shown). Astrocytes, stained for GFAP, were present among the neuronal bundles in the control cultures but were consistently more abundant and more elongated in the IL6R/IL6 chimera treated cultures (not shown).

The more striking difference was observed when pro-oligodendrocytes or immature oligodendrocytes were visualized by staining with anti-sulfatide O4 antibodies. At 6 weeks, the control cultures showed spreading of a number of multipolar O4$^+$ cells among the underlying layer of cells outgrowing from the neurosphere (FIG. 1, upper left panel). In contrast, the cultures with IL6R/IL6 chimera contained a dense network of O4$^+$ cells with considerably more arborization, which formed the majority of the cells in certain areas of the outgrowth and surrounded thickened nerve fibers (FIG. 1 upper right panel). When observed individually, O4 stained oligodendrocytes in the IL6R/IL6 chimera treated cultures could be seen to have grown to a much larger size than in the control cultures.

Example 2

IL6R/IL6 Chimera Enhances the Maturation of Oligodendrocytes to the Myelinating Stage The same procedure as in Example 1 was used, except that the cells growing out from neurospheres were stained with monoclonal antibodies against the myelin basic protein MBP (MAB 386, Chemicon). The accumulation of MBP, a structural myelin protein was clearly observed in the oligodendrocyte network of IL6R/IL6 chimera-treated cultures, but not in the corresponding control cultures (Figure lower panels). The gp130 activator, therefore, not only increased the number and density of the ES-cell derived oligodendrocytes but also their maturation toward the myelinating phenotype. This maturation was further denoted in the IL6R/IL6 chimera-treated cultures by the development of flattened myelin-like membrane sheaths that characterize myelinating oligodendrocytes. This was not seen in the untreated cultures.

The maturation of oligodendrocytes is also characterized by the appearance of the O1 sulfatide glycoside, which replaces the O4-sulfatide seen in immature cells (Schachner et al. 1981). Large O1$^+$ oligodendrocytes with extensive arborization were seen in the IL6R/IL6 chimera-treated cultures, whereas only few and small cells could be found in the corresponding control cultures. IL6RIL6 enhanced the development of mature O1+ oligodendrocytes, whose size was considerably increased as compared to the control cultures (not shown). In other experiments, we also found that the presence of IL6RIL6 during the first 7 days was enough to produce the increase in O1+ cells at the end of the 6 week culture. Furthermore, the stimulating effect of IL6RIL6 was similar in media supplemented with tri-iodothyronine and thyroxine (0.4 ng/ml each; not shown), indicating that the effect of IL6RIL6 is in addition to that of these hormones.

In line with the morphological development of myelin membranes, immunostaining for myelin protein MBP was much higher in the oligodendrocyte network of IL6RIL6-treated cultures at 6 weeks (not shown), than in the control cultures where only weakly labeled and small size cells were seen. Enhancement in MBP+ cells by IL6RIL6 was already observed at 14 days (not shown). The gp130 activator, therefore, not only stimulated differentiation of ES-cell derived oligodendrocyte progenitors but also their maturation toward the myelinating phenotype.

Example 3

IL6R/IL6 Chimera Increases the Number of Oligodendrocyte Progenitors in Short Term Dissociated Cell Cultures Prolonged maintenance of ES cells on the feeder layer gives rise to cell clumps which are enriched for neural progenitors and can be mechanically isolated (Reubinoff et al. 2001). The clumps form floating neurospheres upon culture in serum-free defined EB medium (conditions described in Example 1). Such spheres, prepared from R11 ES cells, were then digested with 5 mg/ml of collagenase/dispase mixture (Sigma, #C3180, St Louis, Mo.) and the dissociated cells were seeded on poly-D-lysine and fibronectin cover slips at a density of $1.5 \times 10^4$ cells/well in 12 well plates. Culture was in defined differentiation medium as in Example 1, FGF-2 and 5 µg/ml laminin being added for the first 4 days and then removed. At this time, half of the wells were supplemented with IL6R/IL6 chimera, 200 ng/ml, and the cultures continued for 18 days. The fixed cells were stained with the Rip monoclonal antibody (from the hybridoma bank, University of Iowa) which labels oligodendrocytes from early stages of development to mature cells but does not stain astrocytes (Friedman et al. 1989). In the cultures treated with IL6R/IL6 chimera, colonies of Rip$^+$ oligodendrocytes were of much larger size and density than in the untreated cultures (not shown). In these relatively short-term cultures of dissociated cells, the oligodendrocytes had short multipolar processes indicating that they are still at the progenitor stage. Hence, IL6R/IL6 chimera acts early on the differentiation of this cell lineage, and would allow to obtain large amounts of ES cell derived oligodendrocyte progenitors suitable for transplantation.

Example 4

Addition of IL6R/IL6 Chimera to EB Cell-Derived Neurospheres Enhances Oligodendrocyte Progenitor Differentiation—A Quantitative Analysis The effects of IL6RIL6 when added to neurospheres cells derived from already preformed EBs were monitored. To produce neurospheres [Zhang 2001 and Reubinoff B E 2001], murine ROSA 11 ES cells, removed from the feeder layer, were induced to form EBs which were then subjected to selection for neural precursors [Okabe et al. 1996] in serum-free medium supplemented with 20 ng/ml FGF-2. Under these conditions one observes the formation of spherical cell aggregates surrounded by outgrowing axons. The cores of these aggregates were dislodged and transferred to suspension culture, in which the floating spheres were maintained in the same selection medium containing FGF-2 for 8 or more days. Dissociation of the floating spheres with trypsin and plating on glass coverslips confirmed that they are mainly composed of small round or elongated bipolar cells, of which 90% are positive for nestin, the intermediate filament protein found in neural precursors (not shown). Very few differentiating cells were seen at this stage, less than 1% staining for GFAP (astrocytes) or βIII-tubulin (neurons) and none staining for the O4 sulfatide marking the progenitors differentiating into oligodendrocytes. In addition cells were examined for stining of the chondroitin sulfate proteoglycan NG2, which was thought to be a specific marker of perinatal early oligodendrocytes progenitors but is now known to be also present in earlier neural multipotent precursors [Belachew et al. 2003]. Up to 10% NG2+ cells were found, but all had a bipolar morphology resembling the other nestin-positive neural precursors present in the neurosphere and not oligodendrocyte progenitors (see below).

To investigate the effect of the gp130 activator IL6RIL6 on differentiation, the floating spheres were placed on glass coverslips coated with poly-D-lysine and fibronectin (PDL-FN), an adherent substratum that favors glial cell development [Rubinoff et al. 1996], and the coverslips were incubated in defined N2 medium with or without IL6RIL6 addition. To promote cell outgrowth, FGF-2 (5 ng/ml) and laminin (2.5 µg/ml) were added during the first 4 days, after which the cultures were continued without these additions. After the first 4 days, the outgrowth had formed a monolayer of GFAP+ cells but no O4+ cells were observed (not shown). On day 7 (i.e. three days after removal of FGF), O4+ oligodendrocyte progenitors became apparent in the control cultures (not shown), but their number and their size was much larger in the presence of IL6RIL6. In comparison, the GFAP+ astrocytes surrounding the neurosphere appeared similar in both conditions. Quantitative analysis of the stained cells versus the total cells labeled by DAPI showed that in the absence of IL6RIL6, more than half the cells in the outgrowth were GFAP+ and about 2% were O4+ oligodendrocytes (Table 1). The data show that in the presence of IL6RIL6 the proportion (but not the absolute amount) of GFAP+ cells was actually reduced whereas the percentage of O4+ cells became 6.4-fold higher than in the control conditions. IL6RIL6 not only increased the proportion of O4+ progenitors, but accelerated their differentiation. Thus, at 15 days (not shown), the IL6RIL6-treated cultures showed a marked expansion and branching of the O4+ oligodendrocyte progenitors, which formed a network over the astrocyte layer. Without IL6RIL6, this differentiation was not apparent in the 15 days cultures.

TABLE 1

Effect of IL6RIL6 on oligodendrocyte number and morphology

| Experiment | | Control conditions | With IL6RIL6 | p value |
|---|---|---|---|---|
| 1. | Percent O4+ cells | 2.2 ± 1 | 14.2 ± 5 | 0.004 |
|    | Percent GFAP+ cells | 56.6 ± 18 | 30.6 ± 11 | 0.004 |
| 2. | Percent O4+ cells | 0.8 ± 0.3 | 7.3 ± 1.7 | 0.002 |
|    | Percent NG2+ cells | 4.2 ± 2.3 | 11.6 ± 2.8 | 0.007 |
| 3. | Branch length (μm) | 52 ± 19 | 211 ± 63 | <0.0001 |

Cell counting and measurements were done on microphotographs using the AlphaEase software. The p values were calculated by the Student's two-tailed t-test.

In another experiment, the outgrowing cells were double stained for NG2 and O4 to compare the effect on early and late progenitors respectively. To facilitate quantitative analysis in these 19-days cultures, the cells were observed at higher magnification which allowed to visualize clearly the increase both in number and in size of the O4+ progenitors produced by IL6RIL6 treatment. The percentage of O4+ cells rose from 0.8 to 7.3%, or 9.1-fold in response to the cytokine (Table 1). The percentage of NG2+ cells was also increased in response to IL6RIL6 but only by 2.7-fold (Table 1). The higher increment of O4+ cells suggests that the main effect of IL6RIL6 may be on the transition from NG2+ early progenitors to more differentiated O4+ cells. When examined at 7 days, the increase in NG2+ cells was similar (percentage increase of 2.5-fold). Although NG2 may be also present in multipotent neural progenitors [Belachew et al. 2003], the NG2+ cells in the outgrowth were mostly multipolar or branched (not shown) as typical for oligodendrocyte progenitors. Moreover, the size of the multipolar and branched NG2+ cells was larger in the IL6RIL6-treated cultures. Hence, although less pronounced than for O4, the enhancement of NG2+ early progenitors was reproducibly observed. On the other hand, when the cultures were stained for tubulin-βIII we did not observe significant changes in the density of the neuron axonal network in the outgrowth surrounding the neurospheres (not shown). This makes it unlikely that the effect of IL6RIL6 on oligodendrocyte differentiation would be a secondary effect resulting from an increase in the axon network.

Example 5

IL6RIL6 Enhances Oligodendrocyte Lineage-Specific Gene Expression

Figure 2:
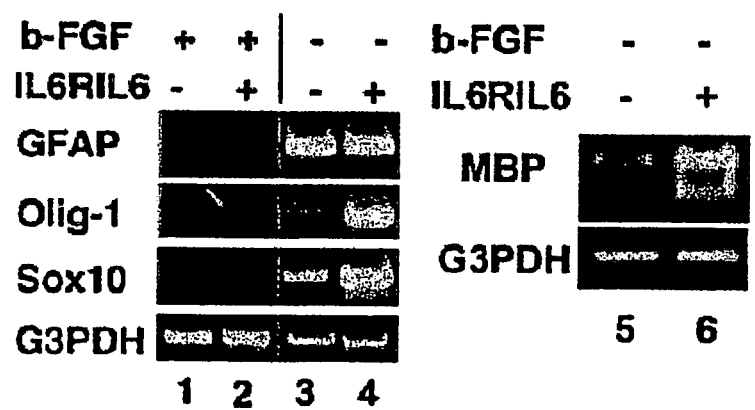
FIG. 2 Shows enhanced expression of oligodendrocyte lineage specific gene by IL6RIL6.

Olig-1 is a transcription factor of the bHLH group, with a restricted expression seen in the oligodendrocyte lineage but not in astrocytes or other glial cells [Zhou et al 2000, Wegner et al. 2001]. Olig-1 is expressed early and appears specifically required for the development and maturation of oligodendrocytes [Lu et al. 2002]. Sox10 is also expressed early in the oligodendrocyte lineage [Wegner et al. 2001] and is a transcription factor acting on the promoters of myelin genes [Slutsky et al. 2003, Stolt et al. 2002]. The expression of these oligodendrocyte marker genes and of the astrocyte marker GFAP was examined by RT-PCR. We first analyzed RNA extracted from the spherical aggregates formed in the EB cultures after selection in serum-free medium with 20 ng/ml FGF-2 for 12 days. Little expression of Olig-1, Sox10 or GFAP RNA was detected in these spherical aggregates even when treated with IL6RIL6 (FIG. 2, lanes 1,2). When RNA was extracted from outgrowing neurospheres cultured under the differentiation conditions on PDL-FN (four days with 5 ng/ml FGF-2 and 2.5 μg/ml laminin and then four more days without these additions), expression of the three marker genes was observed (lane 3). Addition of IL6RIL6 for the last 4 days of this differentiation culture produced a marked increase in Olig-1 and Sox-10, whereas GFAP was unaffected (lane 4). Furthermore, an induction of MBP RNA was observed in response to IL6RIL6 (lanes 5,6). Photometric scanning indicated increases of up to 20-fold for Olig-1 and 7.6-fold for Sox-10 in response to IL6RIL6. In these short term cultures, MBP was increased 3-fold. These gene expression profiles support the conclusion that the gp130 activator exerts enhancing effects on early phases of cell differentiation along the oligodendrocyte lineage (as denoted by Sox-10 and Olig-1 expression), as well as on the maturation toward myelinating MBP-expressing oligodendrocytes.

Example 6

Oligodendrocytes Differentiation from Dissociated Neurosphere Cells

Previous work examined cells that outgrow from the neurospheres. Differentiation can be studied only in part of the cells in the culture, while the neurosphere remaining in the center forms a mass of cells that cannot be well examined. It was, therefore, important to see if the effect of IL6RIL6 could be demonstrated on cells isolated from the neurospheres. We used trypsin digestion to dissociate the neurosphere cells, and plated the dissociated cells on the adherent substrate. After testing a number of experimental conditions, we found conditions suitable to observe the differentiation of oligodendrocytes.

ES cells-derived neurospheres were maintained in suspension cultures in defined medium with 20 ng/ml FGF-2, and then supplemented for 3 days with 20 ng/ml of PDGF and EGF. The neurospheres were harvested and treated with 0.05% trypsin-EDTA and the dissociated cells were plated on coverslips coated poly-ornithine in N2 medium. During the first 3 days, FGF-2 was added at 10 ng/ml and then the growth factor was removed and the culture continued for 10 days. IL6RIL6 was added for the last 3 days at 100 ng/ml. In the control cultures, without IL6RIL6, a few small oligodendrocytes were observed. Treatment with IL6RIL6 cultures resulted in the formation of very large and highly branched oligodendrocytes, exhibiting large myelin membranes (not shown). The surrounding cells were mainly neurons and astrocytes (not shown). These conditions should allow study of gene expression without interference from the remaining neurosphere cell mass.

Example 7

IL6R/IL6 Chimera Enhances the Differentiation of Human Oligodendrocyte Progenitors The human EB and neurospheres are prepared as described by Zhang et al (2001) Briefly, human ES cell lines derived from H1 and H9.2 (as described by Amit et al. 2000) are propagated on a feeder layer of irradiated mouse embryonic fibroblasts (as described by (Thomson et al. 1998). To initiate differentiation, ES colonies are detached and grown as embryoid bodies for four days. The EB are then cultured in a tissue culture treated flask in a chemical defined medium, as described by (Zhang et al. 1999; Zhang et al. 2000; Zhang et al. 2001). After five to seven days in culture with FGF the EB cells generate flattened cells and also an increasing number of small, elongated cells. By seven days the small elongated cells generate rosette formations (or neurospheres). Treatment of dispase leads to preferential detachment of the neurospheres.

The neurospheres are picked and adhered onto glass cover slips coated with poly-D-lysine and fibronectin, a substrate that favors glial cell development (Reubinoff et al. 2001) and supplemented with pure IL6R/IL6 chimera, 200 ng/ml as described in Example 1. Numerous neuronal processes grew out of the spheres, forming axonal bundles that is visualized by immunostaining for βIII-tubulin.

Pro-oligodendrocytes or immature oligodendrocytes are visualized by staining with anti-sulfatide O4 antibodies. After 2-6 weeks, the control cultures (without IL6R/IL6 chimera) show spreading of a number of small multipolar $O4^+$ cells among the underlying layer of cells outgrowing from the neurosphere. In contrast, the cultures with IL6R/IL6 chimera contain a dense network of $O4^+$ cells with considerably more arborization. Staining with antibodies for MBP demonstrates that the IL6R/IL6 chimera promotes the myelinating activity of the cells.

Example 8

ES Cell Cultures and Neurospheres Production

The murine ES cell line ROSA 11 [Friedrich and Soriano 1991] was maintained as before [Li et al. 2001]. The cells were removed from the feeder layer with 0.05% trypsin and transferred without LIF to tissue culture plates in ES1 medium (DMEM/F12 with 15% fetal calf serum (FCS), 1% glutamine, 0.1 mM β-mercapto-ethanol, 2 µg/ml Heparin) with 4 ng/ml of FGF-2. Media were from Gibco/Invitogen and were replenished daily. After 2 days, the culture was treated with 0.2% dispase (Gibco/Invitrogen) for 15 min at 37° C. and the clumps were reseeded into 9 cm tissue culture dishes in ES1 medium lacking FGF. After 4 days, clumps of differentiating embryoid bodies (EB) cells were seen, loosely bound to the dish by the intermediate of a few attached cells. The clumps, easily harvested using a needle, were transferred to new tissue culture dishes and cultured for another day in ES1 medium to facilitate attachment. Afterwards, selection for survival and growth of neural precursors [Okabe et al. 1996] was achieved using EB defined medium (DMEM/F12, 25 µg/ml insulin, 100 mg/ml transferrin, 60 µM putrescine, 30 nM sodium selenite, 2 µg/ml heparin, 20 mM progesterone) with 20 ng/ml of FGF-2. Medium was changed every two days. After 8-10 days, the cores of spherical aggregates containing neural precursors as identified by surrounding radiating axons, were picked up with a needle. These spherical aggregates were then transferred into bacterial culture plates (Sterilin) with the same EB defined medium with 20 ng/ml FGF-2 and kept in suspension for at least 8 days. During the suspension culture, many cells detached from the aggregates and the latter acquired a regular shape typical of neurospheres [Ben-Hur et al. 1998]. Spheres expanding to more than 0.5 mm diameter were cut into two before reseeding in suspension for longer cultures. The composition of the floating neurospheres was examined after complete dissociation with 0.25% trypsin-EDTA, by plating 25,000 cells on coverslips for immunostaining (as below).

Example 9

Cell Differentiation Assay

Four neurospheres from the suspension cultures were deposited on each glass coverslip pre-coated with a solution of 20 µg/ml poly-D-lysine, 250 µg/ml fibronectin, which were then placed into wells of 12-well plates in differentiation N2 medium (DMEM/F12 with 5 µg/ml insulin, 100 µg/ml transferrin, 16.1 µg/ml putrescine, 5.2 ng/ml selenite and 6.3 ng/ml progesterone—all added as 1% N2 supplement from Gibco). Laminin 2.5 µg/ml and FGF-2 5 ng/ml were added for the first 4 days to facilitate attachment, and then removed (laminin was omitted in some experiments without altering the results). Half of the wells were supplemented with IL6RIL6 chimera, 100 or 200 ng/ml, produced in CHO cells and purified as before [Chebath Fischer and Kumar 1997]. The medium was replaced every 3 days, and in prolonged cultures 50 µg/ml ascorbic acid was added to the medium starting at day 21. At indicated times after plating the neurospheres, the cultures were fixed in 4% paraformaldehyde (PFA) and kept in PBS at 4° C. After blocking with 5% normal goat serum (NGS), fixed cells were stained for early progenitors or oligodendroblasts with rabbit polyclonal anti-NG2 (chondroitin sulfate proteoglycan; Chemicon International, Temecula, Calif.; 1:200) for 1 h at room temp (RT) and then Alexa Fluor 566-conjugated goat anti-rabbit antibody (Molecular Probes, Eugene, Oreg.; 1:250). Staining for late progenitors or pre-oligodendrocytes was with anti-sulfatide O4 mouse monoclonal (Mc) IgM antibodies (McAB 345 Chemicon; 1:75) for 1 h at RT and Fluorescein-conjugated goat anti-mouse IgM (Chemicon; 1:50). Immunostaining for GFAP, βIII-tubulin, nestin and MBP was after permeabilization with 0.5% Triton-X100 and blocking with 10% NGS. Staining with mouse Mc anti-GFAP conjugated with the fluorescent Cy3 tag (Sigma, St Louis, Mo.; 1:400) was for 1 h at RT. The mouse Mc IgG Tuj-1 anti-tubulin-bIII (Covance, Berkeley, Calif.; diluted 1:400) was used with goat anti-mouse IgG conjugated with Alexa Fluor 488 (Molecular Probes; 1:250). Staining for myelinating cells was with mouse Mc IgG anti-MBP (McAb 386, Chemicon; 1:400) and Cy3-conjugated affinity purified goat anti-mouse IgG, F(ab')2 fragment specific (Jackson ImmunoResearch Laboratories, West Grove, Pa.; 1:400). Staining for neural precursors was with Mc IgG1 anti-nestin (Rat-401, Developmental Studies Hybridoma Bank at University of Iowa; diluted 1:100) followed by the same Cy3-conjugated IgG as above.

Live cells were stained for O1. After blocking with 5% FCS, anti-O1 mouse IgM Mc antibodies (McAB 344, Chemicon; 1:75) and Fluorescein-conjugated goat anti-mouse IgM (Chemicon; 1:50) were used for 1 h at 37° C. in humidified atmosphere, followed by fixation with 5% acetic acid in methanol. In all cases, the nuclear fluorescent dye DAPI (Sigma; 0.05 µg/ml) was added last. Coverslips were mounted in Mowiol (Calbiochem, LaJolla, Calif.), viewed in an Olympus IX-70 FLA microscope with a DVC-1310C digital camera (DVC, Austin, Tex.) and images processed by Photoshop. Double stained preparations are shown as overlayed images. A manual count program in the AlphaEase software (Alpha Innotech, San Leandro, Calif.) was used to measure sizes and enumerate NG2, O4 and GFAP stained cells, as well as total cell nuclei visualized by DAPI.

Example 10

Gene Expression Assays

Procedures for RNA extraction and RT-PCR for measuring levels of Sox10, GFAP, MBP and glyceraldehyde 3'-phosphodehydrogenase (G3PDH) gene transcripts were as described in detail previously, including the number of cycles and the primers used [Slutsky et al. 2003]. For the Olig-1 gene (accession NM_016968), the primers were: forward, 5'-TGCGCGCGAGAAGGCCGAAG (SEQ ID NO:2) and reverse, 5'-CCCAGCCAGCCCTCACTTG (SEQ ID NO:3). Conditions for PCR amplification: 94° C., 2 minutes then 30 cycles at 94° C., 30 seconds; 56° C., 30 seconds; 72° C., 1 minute. The PCR buffer [Slutsky et al. 2003] was supplemented with 10% DMSO. After gel electrophoresis, the amplified DNA bands were photographed under UV-light, scanned and their intensity was quantified using the AlphaEase spot density software. Band intensity was verified to be in the linear range by varying the amount of PCR reaction loaded on the gels.

REFERENCES

Amit, M., M. K. Carpenter, M. S. Inokuma, C. P. Chiu, C. P. Harris, M. A. Waknitz, J. Itskovitz-Eldor and J. A. Thomson (2000). "Clonally derived human embryonic stem cell lines maintain pluripotency and proliferative potential for prolonged periods of culture." *Dev Biol* 227(2): 271-8.

Bain, G., D. Kitchens, M. Yao, J. E. Huettner and D. I. Gottlieb (1995). "Embryonic stem cells express neuronal properties in vitro." *Dev Biol* 168(2): 342-57.

Barres, B. A., J. F. Burne, B. Holtmann, H. Thoenen, M. Sendtner and M. C. Raff (1996). "Ciliary Neurotrophic Factor Enhances the Rate of Oligodendrocyte Generation." *Mol Cell Neurosci* 8(2/3): 146-56.

Barres, B. A., M. A. Lazar and M. C. Raff (1994). "A novel role for thyroid hormone, glucocorticoids and retinoic acid in timing oligodendrocyte development." *Development* 120(5): 1097-108.

Barres, B. A., M. C. Raff, F. Gaese, I. Bartke, G. Dechant and Y. A. Barde (1994). "A crucial role for neurotrophin-3 in oligodendrocyte development." *Nature* 367(6461): 371-5.

Belachew S, Chittajallu R, Aguirre A A, et al. Postnatal NG2 proteoglycan expressing progenitor cells are intrinsically multipotent and generate functional neurons. J Cell Biol 2003; 161:169-186.

Ben Hur T, Rogister B, Murray K, et al. Growth and fate of nPSA-NCAM+ precursors of the postnatal brain. J Neurosci 1998; 18:5777-5788.

Bensadoun, J. C., L. P. de Almeida, M. Dreano, P. Aebischer and N. Deglon (2001). "Neuroprotective effect of interleukin-6 and IL6/IL6R chimera in the quinolinic acid rat model of Huntington's syndrome." *Eur J Neurosci* 14(11): 1753-61.

Besnard, F., F. Perraud, M. Sensenbrenner and G. Labourdette (1987). "Platelet-derived growth factor is a mitogen for glial but not for neuronal rat brain cells in vitro." *Neurosci Lett* 73(3): 287-92.

Betz, U. A. K., W. Bloch, M. van den Broek, K. Yoshida, T. Taga, T. Kishimoto, K. Addicks, K. Rajewsky and W. Muller (1998). "Postnatally induced inactivation of gp130 in mice results in neurological, cardiac, hematopoietic, immunological, hepatic, and pulmonary defects." *J Exp Med* 188(10): 1955-65.

Blight, A. R. (1985). "Delayed demyelination and macrophage invasion: a candidate for secondary cell damage in spinal cord injury." *Cent Nerv Syst Trauma* 2(4): 299-315.

Bogler, O., D. Wren, S. C. Barnett, H. Land and M. Noble (1990). "Cooperation between two growth factors promotes extended self-renewal and inhibits differentiation of oligodendrocyte-type-2 astrocyte (O-2A) progenitor cells." *Proc Natl Acad Sci USA* 87(16): 6368-72.

Bonni, A., Y. Sun, M. Nadal-Vicens, A. Bhatt, D. A. Frank, I. Rozovsky, N. Stahl, G. D. Yancopoulos and M. E. Greenberg (1997). "Regulation of gliogenesis in the central nervous system by the JAK-STAT signaling pathway." *Science* 278(5337): 477-83.

Brustle, O., K. N. Jones, R. D. Learish, K. Karram, K. Choudhary, O. D. Wiestler, I. D. Duncan and R. D. McKay (1999). "Embryonic stem cell-derived glial precursors: a source of myelinating transplants." *Science* 285(5428): 754-6.

Brustle, O., A. C. Spiro, K. Karram, K. Choudhary, S. Okabe and R. D. McKay (1997). "In vitro-generated neural precursors participate in mammalian brain development." *Proc Natl Acad Sci USA* 94(26): 14809-14.

Bunge, R. P., W. R. Puckett, J. L. Becerra, A. Marcillo and R. M. Quencer (1993). "Observations on the pathology of human spinal cord injury. A review and classification of 22 new cases with details from a case of chronic cord compression with extensive focal demyelination." *Adv Neurol* 59: 75-89.

Cao, Q., R. L. Benton and S. R. Whittemore (2002). "Stem cell repair of central nervous system injury." *J Neurosci Res* 68(5): 501-10.

Chebath, J., D. Fischer, A. Kumar, J. W. Oh, O. Kolett, T. Lapidot, M. Fischer, S. Rose-John, A. Nagler, S. Slavin and M. Revel (1997). "Interleukin-6 receptor-interleukin-6 fusion proteins with enhanced interleukin-6 type pleiotropic activities." *European Cytokine Network* 8(4): 359-65.

Deglon, N., J. L. Tseng, J. C. Bensadoun, A. D. Zurn, Y. Arsenijevic, L. Pereira de Almeida, R. Zufferey, D. Trono and P. Aebischer (2000). "Self-inactivating lentiviral vectors with enhanced transgene expression as potential gene transfer system in Parkinson's disease." *Hum Gene Ther* 11(1): 179-90.

Fraichard, A., O. Chassande, G. Bilbaut, C. Dehay, P. Savatier and J. Samarut (1995). "In vitro differentiation of embryonic stem cells into glial cells and functional neurons." *J Cell Sci* 108 (Pt 10): 3181-8.

Friederich G, Soriano P. Promoter traps in embryonic stem cells: a genetic screen to identify and mutate developmental genes in mice. Genes Dev 1991; 5:1513-1523.

Friedman, B., S. Hockfield, J. A. Black, K. A. Woodruff and S. G. Waxman (1989). "In situ demonstration of mature oligodendrocytes and their processes: an immunocytochemical study with a new monoclonal antibody, rip." *Glia* 2(5): 380-90.

Gard, A. L., W. C. Williams, 2nd and M. R. Burrell (1995). "Oligodendroblasts distinguished from O-2A glial progenitors by surface phenotype (O4+GalC−) and response to cytokines using signal transducer LIFR beta." *Dev Biol* 167(2): 596-608.

Gledhill, R. F., B. M. Harrison and W. I. McDonald (1973). "Pattern of remyelination in the CNS." *Nature* 244(5416): 443-4.

Gottlieb, D. I. (2002). "Large-scale sources of neural stem cells." *Annu Rev Neurosci* 25: 381-407.

Griffiths, I. R. and M. C. McCulloch (1983). "Nerve fibres in spinal cord impact injuries. Part 1. Changes in the myelin sheath during the initial 5 weeks." *J Neurol Sci* 58(3): 335-49.

Haggiag, S., J. Chebath and M. Revel (1999). "Induction of myelin gene expression in Schwann cell cultures by an interleukin-6 receptor-interleukin-6 chimera." *FEBS Lett* 457(2): 200-4.

Haggiag, S., P. L. Zhang, G. Slutzky, V. Shinder, A. Kumar, J. Chebath and M. Revel (2001). "Stimulation of myelin gene expression in vitro and of sciatic nerve remyelination by interleukin-6 receptor-interleukin-6 chimera." *J Neurosci Res* 64(6): 564-74.

Johe, K. K., T. G. Hazel, T. Muller, M. M. Dugich-Djordjevic and R. D. McKay (1996). "Single factors direct the differentiation of stem cells from the fetal and adult central nervous system." *Genes Dev* 10(24): 3129-40.

Kahn, M. A. and J. De Vellis (1994). "Regulation of an oligodendrocyte progenitor cell line by the interleukin-6 family of cytokines." *Glia* 12(2): 87-98.

Kordower, J. H., J. Bloch, S. Y. Ma, Y. Chu, S. Palfi, B. Z. Roitberg, M. Emborg, P. Hantraye, N. Deglon and P. Aebischer (1999). "Lentiviral gene transfer to the nonhuman primate brain." *Exp Neurol* 160(1): 1-16.

Lanza, R. P., J. B. Cibelli and M. D. West (1999). "Human therapeutic cloning." *Nat Med* 5(9): 975-7.

Levine, J. M., R. Reynolds and J. W. Fawcett (2001). "The oligodendrocyte precursor cell in health and disease." *Trends Neurosci* 24(1): 39-47.

Li, X., Y. Chen, S. Scheele, E. Arman, R. Haffner-Krausz, P. Ekblom and P. Lonai (2001). "Fibroblast growth factor signaling and basement membrane assembly are connected during epithelial morphogenesis of the embryoid body." *J Cell Biol* 153(4): 811-22.

Lillien, L. E., M. Sendtner and M. C. Raff (1990). "Extracellular matrix-associated molecules collaborate with ciliary neurotrophic factor to induce type-2 astrocyte development." *J Cell Biol* 111(2): 635-44.

Liu, S., Y. Qu, T. J. Stewart, M. J. Howard, S. Chakrabortty, T. F. Holekamp and J. W. McDonald (2000). "Embryonic stem cells differentiate into oligodendrocytes and myelinate in culture and after spinal cord transplantation." *Proc Natl Acad Sci USA* 97(11): 6126-31.

Lu Q R, Sun T, Zhu Z, et al. Common developmental requirement for Olig function indicates motor neuron/oligodendrocyte connection. Cell 2002; 109:75-86.

Marmur, R., J. A. Kessler, G. Zhu, S. Gokhan and M. F. Mehler (1998). "Differentiation of oligodendroglial progenitors derived from cortical multipotent cells requires extrinsic signals including activation of gp130/LIFbeta receptors." *J Neurosci* 18(23): 9800-11.

Martin, G. R. and M. J. Evans (1975). "Differentiation of clonal lines of teratocarcinoma cells: formation of embryoid bodies in vitro." *Proc Natl Acad Sci USA* 72(4): 1441-5.

Mayer, M., K. Bhakoo and M. Noble (1994). "Ciliary neurotrophic factor and leukemia inhibitory factor promote the generation, maturation and survival of oligodendrocytes in vitro." *Development* 120(1): 143-53.

McDonald, J. W., X. Z. Liu, Y. Qu, S. Liu, S. K. Mickey, D. Turetsky, D. I. Gottlieb and D. W. Choi (1999). "Transplanted embryonic stem cells survive, differentiate and promote recovery in injured rat spinal cord." *Nat Med* 5(12): 1410-2.

Nakashima, K., S. Wiese, M. Yanagisawa, H. Arakawa, N. Kimura, T. Hisatsune, K. Yoshida, T. Kishimoto, M. Sendtner and T. Taga (1999). "Developmental requirement of gp130 signaling in neuronal survival and astrocyte differentiation." *J Neurosci* 19(13): 5429-34.

Novick, D., H. Engelmann, D. Wallach, O. Leitner, M. Revel and M. Rubinstein (1990). "Purification of soluble cytokine receptors from normal human urine by ligand-affinity and immunoaffinity chromatography." *J Chromatogr* 510: 331-7.

Okabe, S., K. Forsberg-Nilsson, A. C. Spiro, M. Segal and R. D. McKay (1996). "Development of neuronal precursor cells and functional postmitotic neurons from embryonic stem cells in vitro." *Mech Dev* 59(1): 89-102.

Pluchino, S., A. Quattrini, E. Brambilla, A. Gritti, G. Salani, G. Dina, R. Galli, U. Del Carro, S. Amadio, A. Bergami, R. Furlan, G. Comi, A. L. Vescovi and G. Martino (2003). "Injection of adult neurospheres induces recovery in a chronic model of multiple sclerosis." *Nature* 422(6933): 688-94.

Raff, M. C. (1989). "Glial cell diversification in the rat optic nerve." *Science* 243(4897): 1450-5.

Reubinoff, B. E., P. Itsykson, T. Turetsky, M. F. Pera, E. Reinhartz, A. Itzik and T. Ben-Hur (2001). "Neural progenitors from human embryonic stem cells." *Nat Biotechnol* 19(12): 1134-40.

Reynolds, B. A. and S. Weiss (1996). "Clonal and population analyses demonstrate that an EGF-responsive mammalian embryonic CNS precursor is a stem cell." *Dev Biol* 175(1): 1-13.

Rogister, B., T. Ben-Hur and M. Dubois-Dalcq (1999). "From neural stem cells to myelinating oligodendrocytes." *Mol Cell Neurosci* 14(4-5): 287-300.

Schachner, M., S. K. Kim and R. Zehnle (1981). "Developmental expression in central and peripheral nervous system of oligodendrocyte cell surface antigens (O antigens) recognized by monoclonal antibodies." *Dev Biol* 83(2): 328-38.

Shamblott, M. J., J. Axelman, S. Wang, E. M. Bugg, J. W. Littlefield, P. J. Donovan, P. D. Blumenthal, G. R. Huggins and J. D. Gearhart (1998). "Derivation of pluripotent stem cells from cultured human primordial germ cells." *Proc Natl Acad Sci USA* 95(23): 13726-31.

Shihabuddin, L. S., J. Ray and F. H. Gage (1999). "Stem cell technology for basic science and clinical applications." *Arch Neurol* 56(1): 29-32.

Slutsky, S. G., A. K. Kamaraju, A. M. Levy, J. Chebath and M. Revel (2003). "Activation of myelin genes during transdifferentiation from melanoma to glial cell phenotype." *J Biol Chem* 278(11): 8960-8.

Stankoff, B., M. S. Aigrot, F. Noel, A. Wattilliaux, B. Zalc and C. Lubetzki (2002). "Ciliary neurotrophic factor (CNTF) enhances myelin formation: a novel role for CNTF and CNTF-related molecules." *J Neurosci* 22(21): 9221-7.

Stolt C C, Rehberg S, adler M, et al. Terminal differentiation of myelin-forming oligodendrocytes depends on the transcription factor Sox 10. Genes Dev 2002; 16:165-170.

Taga, T. and T. Kishimoto (1997). "Gp130 and the interleukin-6 family of cytokines." *Annu Rev Immunol* 15: 797-819.

Thomson, J. A., J. Itskovitz-Eldor, S. S. Shapiro, M. A. Waknitz, J. J. Swiergiel, V. S. Marshall and J. M. Jones (1998). "Embryonic stem cell lines derived from human blastocysts." *Science* 282(5391): 1145-7.

Thomson, J. A., J. Kalishman, T. G. Golos, M. Durning, C. P. Harris, R. A. Becker and J. P. Hearn (1995). "Isolation of a primate embryonic stem cell line." *Proc Natl Acad Sci USA* 92(17): 7844-8.

Thomson, J. A., J. Kalishman, T. G. Golos, M. Durning, C. P. Harris and J. P. Hearn (1996). "Pluripotent cell lines derived from common marmoset (*Callithrix jacchus*) blastocysts." *Biol Reprod* 55(2): 254-9.

Tropepe, V., S. Hitoshi, C. Sirard, T. W. Mak, J. Rossant and D. van der Kooy (2001). "Direct neural fate specification from embryonic stem cells: a primitive mammalian neural stem cell stage acquired through a default mechanism." *Neuron* 30(1): 65-78.

Valerio, A., M. Ferrario, M. Dreano, G. Garotta, P. Spano and M. Pizzi (2002). "Soluble interleukin-6 (IL-6) receptor/IL-6 fusion protein enhances in vitro differentiation of purified rat oligodendroglial lineage cells." *Mol Cell Neurosci* 21(4): 602-15.

Wegner M. Expression of transcription factors during oligodendroglial development. Microsc Res Tech 2001; 52:746-752.

Zhang, S. C., B. Ge and I. D. Duncan (1999). "Adult brain retains the potential to generate oligodendroglial progenitors with extensive myelination capacity." *Proc Natl Acad Sci USA* 96(7): 4089-94.

Zhang, S. C., B. Ge and I. D. Duncan (2000). "Tracing human oligodendroglial development in vitro." *J Neurosci Res* 59(3): 421-9.

Zhang, S. C., C. Lundberg, D. Lipsitz, L. T. O'Connor and I. D. Duncan (1998). "Generation of oligodendroglial progenitors from neural stem cells." *J Neurocytol* 27(7): 475-89.

Zhang, S. C., M. Wernig, I. D. Duncan, O. Brustle and J. A. Thomson (2001). "In vitro differentiation of transplantable neural precursors from human embryonic stem cells." *Nat Biotechnol* 19(12): 1129-33.

Zhou Q, Wang S, Anderson D J. Identification of a novel family of oligodendrocyte lineage-specific basic helix-loop-helix transcription factors. Neuron 2000; 25:331-343.

The invention claimed is:

1. A method for generating $O1^+$ and/or $O4^+$ oligodendrocytes, said method comprising
   growing neurosphere (NS) cells in a culture medium that promotes preferential differentiation of NS cells into $O1^+$ and/or $O4^+$ oligodendrocytes,
   said culture medium comprising one or more, IL6R/IL6 chimeras, and
   wherein said culture medium specifically enhances differentiation into the $O1^+$ and/or $O4^+$ oligodendrocyte lineage, thereby causing the NS cells to preferentially differentiate along the oligodendrocyte lineage into $O1^+$ and/or $O4^+$ oligodendrocytes.

2. The method according to claim 1, wherein the cells are dissociated NS cells.

3. The method according to claim 1, wherein oligodendrocytes of $O1^+$ lineage are generated.

4. The method according to claim 1, wherein oligodendrocytes of $O4^+$ lineage are generated.

5. The method in accordance with claim 1, wherein said NS cells are human NS cells.

6. The method according to claim 1, wherein said culture medium promotes myelinating activity.

7. The method according to claim 1, wherein said growth in said culture medium produces $O1^+$ and/or $O4^+$ oligodendrocytes with large myelin membranes and more aborization, as compared to control NS cells not grown in said culture medium.

8. The method according to claim 1, wherein only NS cells are present in the growing in the culture medium step.

9. The method according to claim 1, wherein dissociated NS cells are utilized in the growing in the culture medium step.

10. The method in accordance with claim 1, wherein said one or more IL6R/IL6 chimeras are the only growth or differentiation agent present in the culture medium to cause NS cells to differentiate along the oligodendrocyte lineage into $O1^+$ and/or $O4^+$ oligodendrocytes.

11. The method of claim 4 wherein if cell outgrowth in N2 medium is stimulated with FGF-2 and laminin, the percentage $O4^+$ cells in the outgrowth after 19 days is at least 7.3%.

* * * * *